United States Patent [19]

Johnson

[11] 3,948,606

[45] Apr. 6, 1976

[54] PROGRAMMED TEST TUBE RACK FOR MANUALLY PERFORMING MEDICAL DIAGNOSTIC ASSAYS

[76] Inventor: Derrold D. Johnson, 1145 NW. 185 Terrace, Miami, Fla. 33169

[22] Filed: Jan. 26, 1973

[21] Appl. No.: 326,975

[52] U.S. Cl. ................ 23/259; 23/230 B; 23/230.3; 23/253 R; 23/292; 35/18 R; 128/2 R; 424/1.5

[51] Int. Cl.[2] ...................... B01L 9/06; G01N 33/16

[58] Field of Search ............. 23/230 B, 253 R, 259; 35/18 R

[56] References Cited

UNITED STATES PATENTS

| | | | |
|---|---|---|---|
| 3,193,359 | 7/1965 | Baruch | 23/259 |
| 3,239,312 | 3/1966 | Bell | 23/259 X |
| 3,544,272 | 12/1970 | Vails | 23/259 X |
| 3,554,703 | 1/1971 | Moss | 23/253 R |
| 3,607,097 | 9/1971 | Auphan | 23/259 |
| 3,618,836 | 11/1971 | Bushnell | 35/18 R |
| 3,624,223 | 11/1971 | Smythe | 23/230 B X |
| 3,687,632 | 8/1972 | Natelson | 23/259 |
| 3,713,771 | 1/1973 | Taylor | 23/259 X |
| 3,778,232 | 12/1973 | McMorrow, Jr. | 23/253 R |

*Primary Examiner*—Morris O. Wolk
*Assistant Examiner*—Sidney Marantz
*Attorney, Agent, or Firm*—Ernest H. Schmidt

[57] ABSTRACT

A test tube rack having columns and rows for manually performing medical diagnostic assays which require various sequential operations. The top face of the rack has indicia such as color strips and written directions to provide a program of operations which is to be followed in a particular assay. The individual test tubes are manually progressed in columns from row to row as the programmed sequence of operations is carried out. The top face may be replaced by other top plates programmed for other different assays.

9 Claims, 2 Drawing Figures

PROGRAMMED TEST TUBE RACK FOR MANUALLY PERFORMING MEDICAL DIAGNOSTIC ASSAYS

Figure 1:
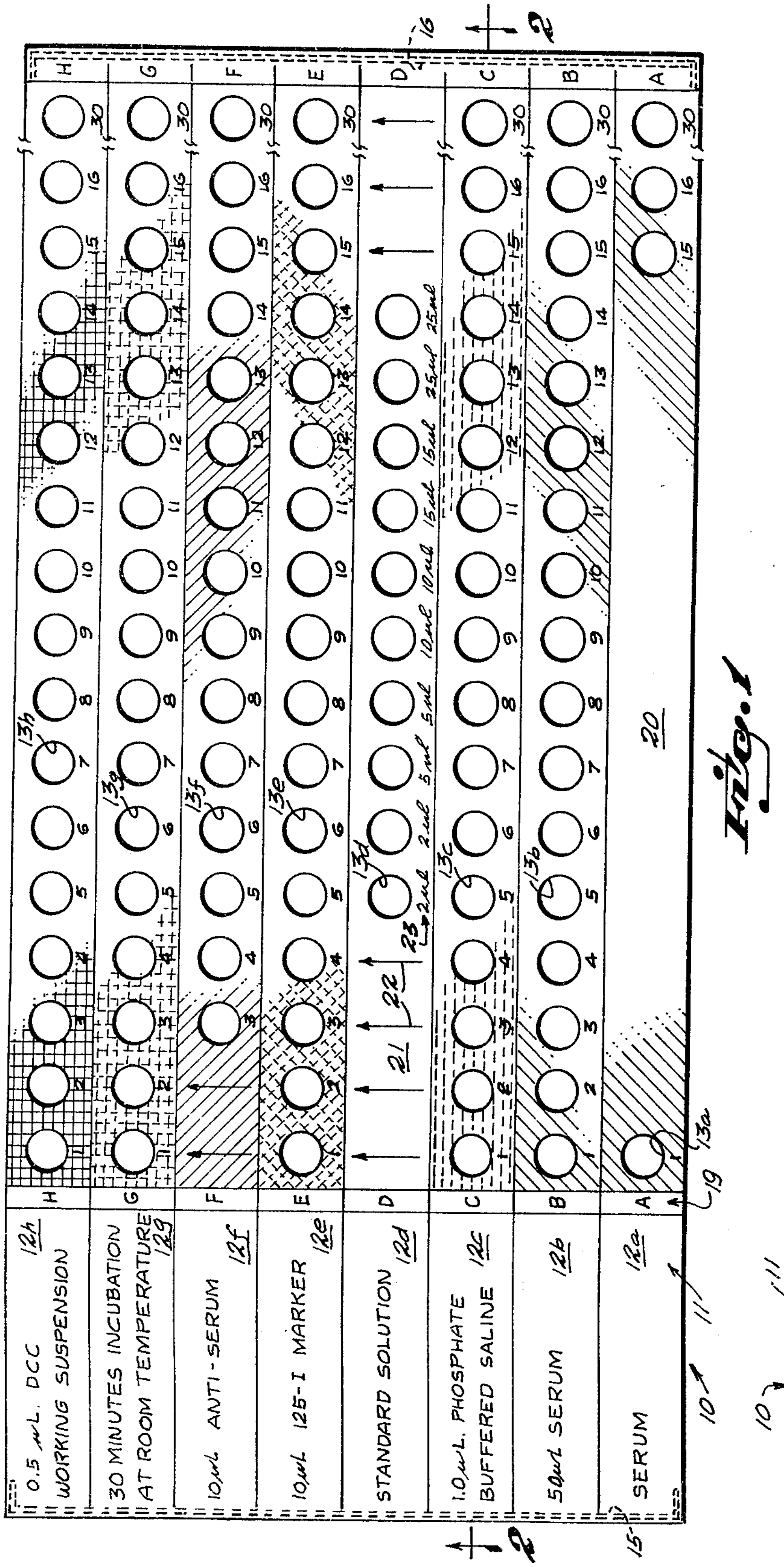

This invention relates to laboratory techniques for the analysis of physiological samples such as blood plasma or serum in medical diagnosis, and is directed particularly to improvements in the method and means for performing such analyses.

Heretofore, in the performance of blood tests, analyses or assays of one kind or another in medical diagnosis or eveluation, it has been common practice to perform the various steps or operations on patient's samples, comparison standards and the like in marked test tubes in ordinary unmarked test tube racks, the tubes not being moved as the various steps comprising the analysis were performed. With this method, if the procedure of the particular analysis happened to be involved or complicated, it was necessary for the technician to refer constantly to the schedule of operations to avoid mistakes. The more complicated the procedure of any particular analysis, the more likelihood there was of the technician making a mistake. For example, radio assays and radio-immuno assays require the performance of four or more operations on each test tube. Such operations include the addition of reagents (buffer solutions, radioactive markers, seperating agents, etc.) the addition of standard solutions, incubation at different temperatures (4°C., 25°., 37°., etc.), and splitting of test tube contents into two or more test tubes. Selected test tubes bypass certain operations, as dictated by the assay protocol. The number of test tubes handled is large, standards requiring from 10 to 24 test tubes and each patient sample requiring from 2 to 8 test tubes. These quantities, moreover, double at the separation operation in many assays. Heretofore, these assays were carried out in plain test tube racks, with constant reference to written instructions or the assay protocol. With such complexity of assay procedure it will readily be understood that the operator, if interrupted for any reason such as by a telephone call, or if he should momentarily relax his concentration on the procedure, could easily make such mistakes as double pipepetting into one tube, or skipping a tube entirely in conducting the assay. This invention, accordingly, has for its principal object the provision of a novel method and means for the performance of medical diagnostic assays, particular radio-assays of the type utilizing radioactive isotopes, that minimizes the likelihood of error, while at the same time simplifying the procedure on the part of the technician or operator performing the assay.

An object of the invention is to provide a method for the performance of medical assays which involves the use of a single test tube rack having a plurality of test tube position openings or supporting stations arranged in a plurality of aligned rows, each row being representative of a step to be performed in the program or schedule of the assay, and each row of which comprises a plurality of test tube openings or support stations for the accommodation of each of the test tube samples, standards and the like used in the assay procedure.

A more particular object of the invention is to provide a radio-assay rack of the character above-described which will be specific to the performance of any particular radio-assay, and for which purpose comprises the precise number of rows of test tube stations required for the particular assay, and further comprises the precise plurality of test tube stations required in each row, and wherein each row is color-coded to indicate a particular corresponding operation to be performed on test tubes stationed along each row as the assay proceeds progressively from row-to-row of the test tube support stations.

Figure 2:
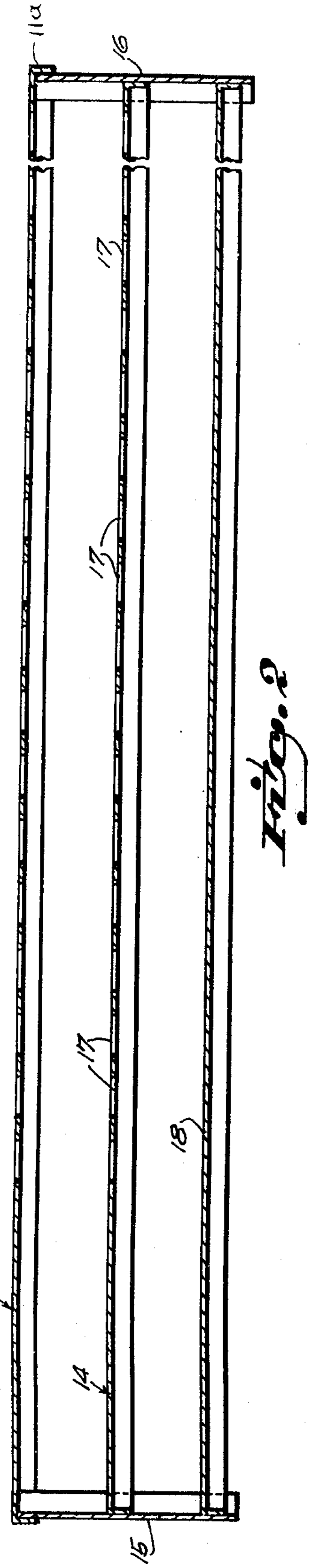

Other objects, features and advantages of the invention will be apparent from the following description when read with reference to the accompanying drawings. In the drawings, wherein like reference numerals denote corresponding parts throughout the several views:

FIG. 1 is a top view of a typical test tube rack embodying the invention; and FIG. 2 is a vertical cross-sectional view taken along the line 2—2 of FIG. 1 and illustrating constructural details of the rack.

Referring now in detail to the drawings, the test tube rack 10 comprising the invention and by means of which the method is carried out comprises a rectangular face panel 11 having a plurality of rows 12*a* through 12*h* extending from side-to-side along the rack from bottom to top respectively, the rows preferably being of equal width. Equidistantly spaced along each row are a plurality of groups of circular test tube openings or stations 13*a* through 13*h*. The test tube openings or station of all of the rows are regularly spaced along their lengths so that individual openings of any row will be in vertical alignment with corresponding openings in any one or more of the other rows.

The face panel 11 is removably secured to a supporting structure comprising a rectangular intermediate locating plate 14 having vertical support wall members 15 and 16 at each end. The face panel is formed with a downwardly-bent peripheral lip 11a adapted to fit in embracing relation over upper end portions of the vertical support wall members 15 and 16, whereby it can readily be removed for selective replacement by other face plates programmed for various other assays, as is hereinbelow more particular described.

The intermediate locating plate 14 is provided with circular openings 17 vertically aligned with each of the various test tube openings in the face panel 11, through which test tubes inserted through any one of the openings in said face panel can pass for locating them in upright position in the rack. Lower end portions of the rack end wall members 15 and 16 are secured to a base plate 18, arranged in spaced parallel relation below the intermediate locating plate 14, which serves as seating means for the lower ends of test tubes placed in the rack.

The test tube rack 10 differs from ordinary test tube racks in that the test tube stations or openings are programmed along each row and from row-to-row in sequential order to simplify the performance of a particular medical diagnostic assay, ordinarily a blood serum or plasma assay involving a plurality of sequentially performed laboratory steps or procedures. Since, because of their relative complexity, the invention is particularly well-suited to use in the performance of radio-assays and radio-immuno assays the rack 10 is illustrated and described herein, by way of example, as typical in carrying out the procedure for the radio-immuno assay of digoxin levels in serum or plasma as developed by the Schwartz/Mann company, a division of Becton, Dickinson and Co. of Orangeburg, New York. To this end, the programming of the assay rack 10, as is hereinbelow more particularly described, is specific to digoxin level assay.

Considering now the programming concept of the invention, it is first to be noted that each row of test tube openings or stations, designated rows "A" through "H" from bottom to top along the column identified by reference numeral 19 in FIG. 1, comprises a step in the procedure to be followed in the particular assay to be performed, and that the programming is such that steps are performed sequentially from row-to-row beginning at the bottom of the rack (row A) and proceeding upwardly until the rack work of the procedure is completed (row H in the example illustrated). Each row is programmed to receive only the test tube or tubes on which an operation is to be performed at that step. To this end, if no test tubes are required at any station or stations along the first or bottom row step of the procedure, such station openings will be omitted or suitably covered or closed off to prevent the insertion of test tubes. Thus, as indicated at 20 in FIG. 1, station openings "2" through "14" are omitted as not required in the initial step of the particular assay procedure. Similarly, if no operation is to be performed at any one or any plurality less than the full complement of test tube stations along any row subsequent to the first row, such station opening or openings will be omitted or covered, as indicated at 21 along row D in FIG. 1, so that in advancing from step "C" to step "D" in the performance of the particular digoxin assay herein described by way of example, the test tubes directly under the omitted openings will skip to aligned openings in the next subsequent row. Vertically-extending arrows 22 marked through omitted test tube station openings serve to further inform the technician that corresponding tubes are to skip a row as tubes along a row are passed to the next row upon completion of an operation called for at the previous row.

As part of the programming each row is definitive of a particular procedure or operation to be performed upon the test tube or tubes stationed therealong and such procedural operation is designated by color code extending along the row. The color code is the same for all assays (Digoxin, Angio-tensin I, Human Placental Lactogen, etc.) so that the operator quickly learns to associate a particular color with a specific operation. The color orange, for example, could always designate the addition of a radioactive solution or suspension; the color grey could always designate the addition of a buffer solution, etc. In the particular embodiment of the invention herein described and illustrated rows A and B may be colored brown to designate serum, row C is colored grey to designate a buffer solution, row D is colored white to designate a standard solution, row E is colored orange to designate the addition of a radioactive solution, row F is colored green to designate the addition of an anti-serum, row G is colored yellow to designate an incubation period at room temperature, and row H is colored black to indicate a separation step. Additionally, the test tube openings or stations along each row are numbered in consecutive order from left to right, so that each test tube as it advances stepwise from row-to-row in the performance of an assay will always bear the same number which number will be marked on each test tube to prevent any possibility of mix-up along a row.

As an additional aid to the technician performing an assay in accordance with the invention, each of the rows 12*a* through 12*h*, besides being color coded to a specific operation as described above, is provided with descriptive matter more particularly describing the operation to be performed. Such descriptive matter, as illustrated, may be printed or otherwise impressed on the face plate along each row and to the left of column 19 in which the row designation letters "A" through "H" are printed. Moreover, if, at any particular row, different sub-operations are to be performed on tubes or on groups of tubes stationed therealong descriptive matter thereof can be placed directly under such tube stations along the row. Thus, as indicated at 23 along row D in the face plate of FIG. 1, it is indicated that 2 $\mu$l. of standard solution are to be pipetted into test tubes 5 and 6; 5 $\mu$l. are to be pipetted into test tubes 7 and 8, etc. in the performance of the step or operation called for in row D.

Considering now, briefly, the overall procedure in the performance of digoxin assay utilizing the programmed rack embodying my invention, standard serum prepared in accordance with the procedure will first be placed in a test tube at station 1 along row "A", patient no. 1 serum will be placed in test tube station 15A, patient no. 2 serum will be placed in test tube station 17A, etc. depending upon the number of patients upon whom the assay is to be simultaneously performed. Empty test tubes will then be placed along row "B", numbered according to their test tubes station position. In accordance with the operation designation of row "B", 50 $\mu$l. of serum will be pipetted from row "A" to row "B", the standard serum being pipetted into test tube numbers 1 through 14 and the patients' serum being pipetted into corresponding test tubes 15, 16, 17, 18 etc. depending upon the number of patients upon whom the assay is being performed. As each test tube receives the designated operation, it is advanced individually to corresponding open stations along row "C" whereat, as indicated, 1.0 $\mu$l. of buffer solution will be pipetted into each of the test tubes. As each test tube receives the designated operation, it is advanced individually to corresponding open stations along row "D" and row "E". Thereafter, test tubes numbered 5 through 14 in row "D" receive the addition of standard solution in the quantities indicated therealong, each test tube being advanced individually to row "E" for the operation step there indicated. It will be noted that test tubes numbered 1 through 4, 15, 16, etc. skip the operation of step "D" and move directly to row "E" positions, whereat all the test tubes will be subjected to the addition, by pipetting, of 10 $\mu$l. of 125-I marker solution, the radioactive agent prepared in accordance with the assay technique. As the test tubes are thus treated, with the exception of tubes 1 and 2, which skip directly to row "G", they are advanced to their corresponding stations along row "F" for receiving 10 $\mu$l. of anti-serum, as called for in this row. The tubes will then be advanced to row "G" and allowed to remain there for a 30 minute incubation period at room temperature. At the termination of the incubation period all test tubes will be advanced to their corresponding positions along row "H" whereat they will be subjected to the addition by pipetting thereto of 0.5 $\mu$l. of dextran coated charcoal (DCC). The use of the rack embodying the invention will be completed at this step, the treated material in the test tube along row "H" now being ready for centrifuging, radiation count and the construction of assay curves in accordance with the assay technique.

With reference to FIG. 1 it will be noted that at least 16 test tube openings or stations are required along each row "A" throuhg "H" to perform the particular digoxin assay herein described by way of example, test tube stations 15 and 16 being used for the serum of a single patient on whom the assay is to be made. Since it is often necessary to perform the same assay on a small number of different patients at the same time the rack 10 is extended in length to accommodate additional pairs of stations for each additional patient to be assayed. Thus, as indicated in FIGS. 1 and 2, the rack will preferably be extended to accommodate for additional stations 17 through 30, allowing for the performance of a digoxin assay on as many as 8 different patients simultaneously. The increased length of the rack thus resulting also better adapts it to use in the performance of other assays of a more complicated nature wherein a greater number of test tube stations along each row is required but wherein it is unlikely that more than 2 or 3 patients would be assayed at the same time. As described above the face panel 11 is removably secured to the supporting structure whereby a set of such face panels, all of the same size but programmed in the manner hereinabove described for the performance of various other assays, particularly the more complicated radio-immuno assays, can be provided for use in combination with a common supporting structure.

While I have illustrated and described herein only one form in which my invention can conveniently be embodied in practice, it is to be understood that this embodiment is presented by way of example only and not in a limiting sense. Thus, while I have illustrated and described the rack as comprising a supporting structure having an intermediate locating plate and vertical support wall members at each end and a base plate, it is to be understood that the rack could also be molded of plastic material formed with blind vertical recesses for the test tube stations, for example, without departing from the teachings of the invention. The invention, in brief, comprises all the embodiments and modifications coming within the scope and spirit of the following claims.

What I claim as new and desire to secure by Letters Patent is:

1. An apparatus for performing medical diagnostic assays requiring the manual performance of a plurality of various operations in sequential order on a group of test tubes, comprising, in combination, a test tube support structure, said test tube support structure having a unitary top face, said top face comprising a plurality of rows of test tube support stations all of which are fixed with respect to said unitary top face, each row having a plurality of laterally spaced and aligned individual test tube stations, the individual stations of each row being in perpendicular alignment with corresponding stations of each of the other rows, the centers of all of the individual stations of all of the rows defining on said top face a grid or pattern of horizontal and vertical lines passing through the centers of all of said stations to permit individual test tubes to be individually manually moved perpendicularly from row to row stepwisely upon the completion of particular assay operations thereupon, one or more of said stations being omitted from one or more of said rows to provide for skipping of certain operations on certain test tubes being manually advanced stepwisely perpendicularly from row to row in the performance of a particular assay, and indicia along each row descriptive of the particular operation to be performed on test tubes stationed along that row in the performance of a particular assay.

2. Medical diagnostic assay apparatus as defined in claim 1, wherein said top face is removably fitted with respect to said test tube support structure to provide for the replacement thereof with other face plates, selectively, having different indicia along each row for the performance of other diagnostic assays.

3. Medical diagnostic assay apparatus as defined in claim 2, wherein said indicia comprises written matter along each row describing the operation to be performed on test tubes stationed along that particular row.

4. Medical diagnostic assay apparatus as defined in claim 2, wherein said top face comprises a panel member, said test tube support stations comprising openings in said panel member for the reception of test tubes, one or more of said station openings being omitted from one or more of said rows to provide for skipping of certain operations on certain test tubes being advanced stepwisely from row-to-row in the performance of the particular assay for which the face panel is programmed.

5. Medical diagnostic assay apparatus as defined in claim 4, wherein the indicia along each row comprises a strip of a particular color, coded to the operation to be performed along that particular row.

6. Medical diagnostic assay apparatus as defined in claim 1, wherein the indicia along each row comprises a strip of a particular color, coded to the operation to be performed along that particular row.

7. Medical diagnostic assay apparatus as defined in claim 6, wherein said indicia further comprises written matter impressed along each row and describing the operation to be performed on test tubes stationed along that particular row.

8. Medical diagnostic assay apparatus as defined in claim 6, wherein said top face comprises a panel member, said test tube support stations comprising openings in said panel member for the reception of test tubes, one or more of said station openings being omitted from one or more of said rows to provide for said skipping of certain operations on certain test tubes.

9. Medical diagnostic assay apparatus as defined in claim 8, wherein said indicia further comprises written matter impressed along each row and describing the operation to be performed on test tubes stationed along that particular row.

* * * * *